United States Patent [19]

Buffet

[11] 4,418,695
[45] Dec. 6, 1983

[54] IMPLANTABLE CARDIAC STIMULATOR HAVING THERAPEUTIC DIAGNOSTIC FUNCTIONS

[76] Inventor: Jacques Buffet, 28 avenue Thiers, 93340 Le Raincy, France

[21] Appl. No.: 235,553

[22] Filed: Feb. 18, 1981

Related U.S. Application Data

[63] Continuation-in-part of Ser. No. 160,168, Jun. 17, 1980, abandoned, which is a continuation of Ser. No. 20,841, Mar. 15, 1979, abandoned.

[30] Foreign Application Priority Data

Mar. 14, 1978 [FR] France ............... 78 07270

[51] Int. Cl.³ .................... A61N 1/36
[52] U.S. Cl. .................... 128/419 PG
[58] Field of Search .............. 128/419 PG, 419 PS

[56] References Cited

U.S. PATENT DOCUMENTS

| | | | |
|---|---|---|---|
| 3,528,428 | 9/1970 | Berkovits | 128/419 PG |
| 3,742,938 | 7/1973 | Stern | 128/419 PT |
| 4,015,609 | 4/1977 | Mensink et al. | 128/419 PS |
| 4,163,451 | 8/1979 | Lesnick et al. | 128/419 PG |
| 4,197,850 | 4/1980 | Schulman et al. | 128/419 PS |
| 4,250,888 | 2/1981 | Grosskopf | 128/706 |

*Primary Examiner*—William E. Kamm
*Attorney, Agent, or Firm*—Robert E. Burns; Emmanuel J. Lobato; Bruce L. Adams

[57] ABSTRACT

An implantable cardiac stimulator having terminals for connections with a cardiac probe comprises an amplifier for receiving and amplifying a signal received from the probe, a band pass filter for filtering the output of the amplifier and a level detector which responds to a predetermined level of the amplified and filtered signal. A logic module comprising a clock, a microprocessor and a memory is connected with the level detector and with a magnetically operable control switch which can be actuated by a permanent magnet outside the body. The stimulator automatically performs the normal therapeutic function of palliating the patients cardiac insufficiencies and also provides means for monitoring operation of the stimulator and the condition and degree of dependency of the patient on the stimulator.

7 Claims, 9 Drawing Figures

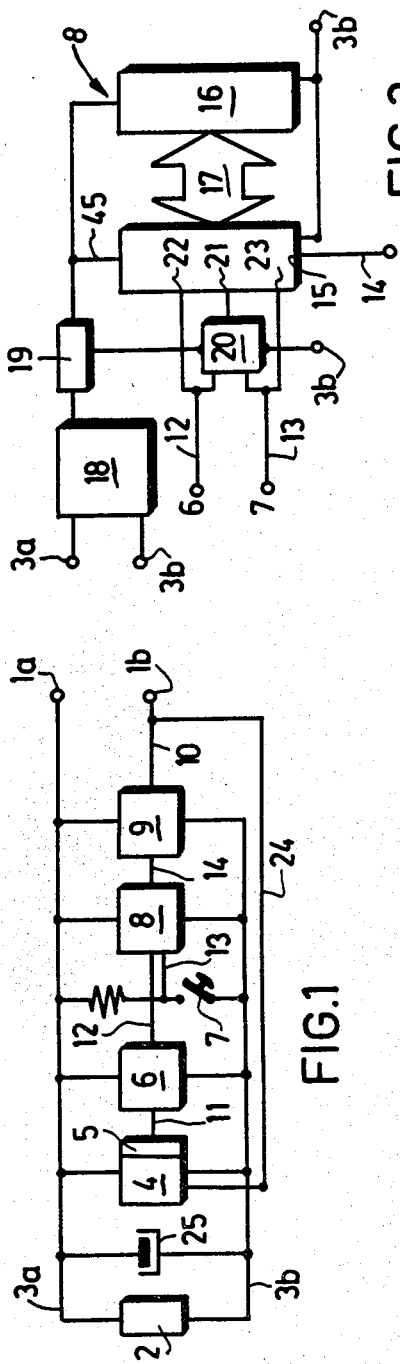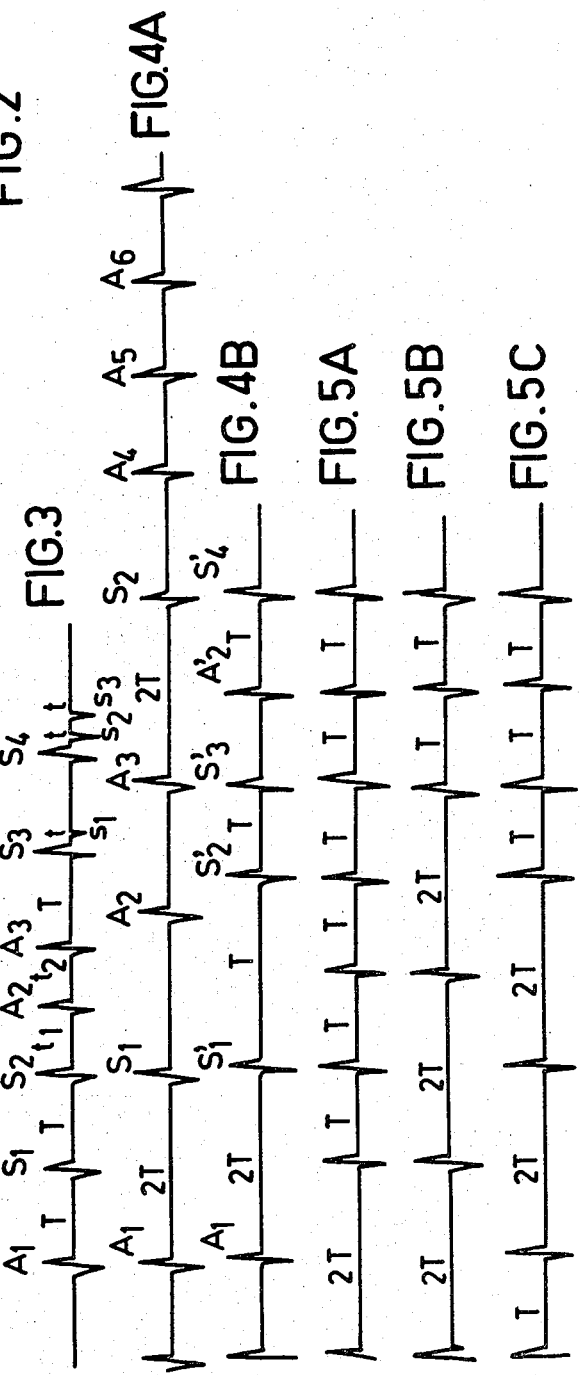

IMPLANTABLE CARDIAC STIMULATOR HAVING THERAPEUTIC DIAGNOSTIC FUNCTIONS

REFERENCE TO PRIOR APPLICATIONS

This application is a continuation-in-part of my application Ser. No. 160,168, filed June 17, 1980 as a Rule 60 continuation of my application Ser. No. 020,841, filed Mar. 15, 1979, both now abandoned.

FIELD OF THE INVENTION

The present invention relates to cardiac stimulators and has specific reference to an implantable cardiac stimulator having not only its normal therapeutic function of automatically stimulating the patient's cardiac insufficiencies but also the additional function of subsequently monitoring the condition and degree of dependency of the patient with respect to the cardiac stimulator performing this therapeutic function. In other words, this stimulator pertains to the category of non-competitive pacemakers comprising, in addition to an oscillator, an electronic circuit designed to sense inherent electrical cardiac activity. The latter is capable of modifying the output of the pacer should a natural contraction of the heart occur within a present time interval.

DESCRIPTION OF THE PRIOR ART

It is nowadays current practice to implant in patients suffering from cardiac insufficiencies stimulators capable of performing a therapeutic function in order to palliate these previously diagnosed troubles. In other cases, a diagnosis is not sufficient for revealing with an adequate certainty the cardiological origin of the troubles observed in the patient. In these assumptions, implanting a stimulator may be as hazardous as not implanting one. Moreover, it is scarcely possible later to check the condition and degree of dependency of the patient with respect to the cardiac stimulator therefore the objective utility of this device.

In an attempt to solve this problem, various completely external and rather bulky recording apparatus has already been proposed. Such apparatus is therefore cumbersome and in most instances the results obtained therewith are not reliable.

SUMMARY OF INVENTION

It is the essential object of the present invention to avoid the above-mentioned inconveniences of prior art devices by providing an implantable cardiac stimulator adapted to be associated with a cardiac probe, this stimulator comprising a case enclosing means for automatically performing the normal therapeutic function of the stimulator in order to palliate the patient's cardiac insufficiencies. Moreover, this stimulator is characterized in that it comprises in the case means capable of subsequently monitoring the condition and the degree of dependency of the patient with respect to the cardiac stimulator performing its therapeutic function, and that the internal monitoring means are controlled for external disconnectable control means.

Other features and advantages of the invention will appear as the following description proceeds with reference to the attached drawing.

BRIEF DESCRIPTION OF THE DRAWING

FIG. 1 is a block diagram illustrating a cardiac stimulator according to the invention;

FIG. 2 is another block diagram illustrating diagrammatically the logic modulus incorporated in the cardiac stimulator;

FIG. 3 is a diagram showing the stimulator operation according to the general program;

FIG. 4A is a diagram showing the possible evolution of a monitoring program;

FIG. 4B is a diagram showing the possible evolution of another monitoring program.

FIGS. 5A, 5B and 5C are three diagrams illustrating registrations obtained by using the stimulator of this invention.

DESCRIPTION OF THE PREFERRED EMBODIMENT

Figure 6:
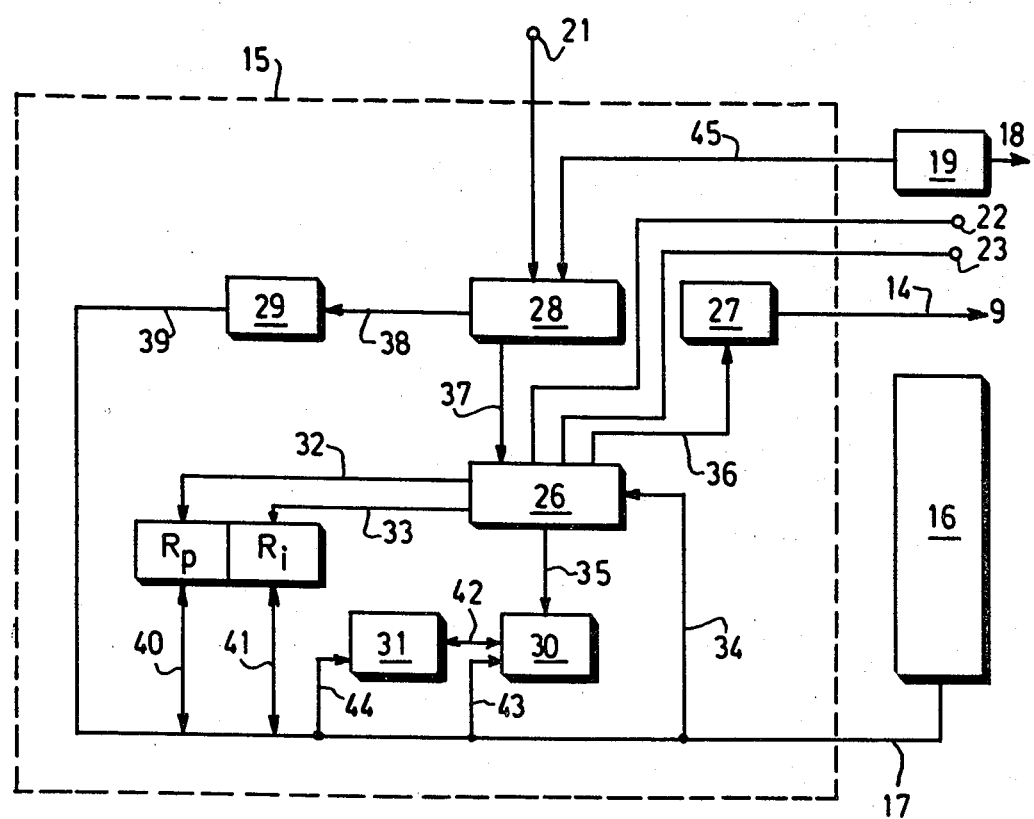
FIG. 6 is a block diagram of a microprocessor control unit of the apparatus.

According to this invention, as illustrated in FIG. 1, there is provided an implantable cardiac stimulator adapted to be associated with a cardiac probe (not shown), which comprises a case containing means for performing automatically the normal therapeutic function of the stimulator in order to palliate the patient's cardiac insufficiencies. This stimulator further comprises within the case means capable of subsequently performing a monitoring function with respect to the condition and the degree of dependency of the patient to the stimulator performing its therapeutic function. External disconnectable means are provided for controlling the means having said monitoring function.

The means performing the therapeutic and monitoring functions comprise a pair of electrodes 1a, 1b adapted to be connected through suitable means to the cardiac probe, a self-contained source 2 of electric current, for example a battery provided with connections 3a and 3b, of which one, for instance connection 3a, is connected to one electrode 1a. Connected in parallel across said connections 3a and 3b are the following elements: a capacitor 25, an amplifier 4 with its filter 5; a level detector 6; a magnetically operable switch 7; a logic module 8, and an output stage 9 coupled by a connection 10 to the other electrode 1b. Connections 11, 12, 13 and 14 link the amplifier 4 and its filter 5 to the level detector 6, the latter to the logic module 8, the magnetic switch 7 also to said logic module 8 and the latter to the output stage 9. The amplifier 4 is also connected by a connection 24 with the electrode 1b.

The function of the amplifier 4 and of its filter is to amplify and filter the signals detected on electrodes 1a and 1b. Its coefficient of voltage amplification is notably of the order of 500. The filter 5 is notably of the band-pass type centered on a frequency equal or close to 60 Hertz.

The level detector 6 is switched on when the output level of amplifier 4 and filter 5 exceeds a predetermined value; for example about 0.5 Volt. As a result, with this device any signal detected on the electrodes and tuned to the band-pass, and of which the amplitude after amplification is greater than the switching threshold of detector 6, will switch on this detector 6.

The function of the logic module 8 to be described more in detail presently is to generate stimulation pulses in synchronism with the output signals from level detector 6.

The function of the output stage 9 is to deliver pulses ganged and shaped as a function of the output signal of the logic module 8 to the electrodes 1a, 1b.

The magnetic switch 7 is of the flexible-blade switch type normally held in its open-circuit position. This relay is adapted to be actuated to its closed-circuit position by means of disconnectable external control means, notably magnetic means, and more particularly a member capable of producing a magnetic field such as a permanent magnet.

As illustrated in FIG. 2, the logic module 8 comprises a microprocessor central unit 15, a memory 16 connected to the central unit 15 by a bus 17 and a clock 18 connected through a voltage doubler 19 to the central unit 15, memory 16 and a logic OR gate 20. The gate 20 is coupled with the switch-off input 21 of the central unit 15 and also to the two indicator inputs 22 and 23. The input of the OR gate 20 is connected through connections 12 and 13 to the level detector 6 and the magnetically operable switch 7. The central unit 15 is, of course, connected at 14 to the output stage 9.

All of the above-described circuits are preferably of the M O S transistorized type. This particular technology is advantageous notably in that the device can operate under relatively very low feed voltages with a low current consumption under low frequency conditions.

The clock 18 is of any known and suitable type, notably in the form of an oscillator consisting of logic inverters and a resistance-capacity circuit. Current is supplied to the clock from the battery by a by-pass capacitor. Its oscillation frequency is dependent upon the charging time of the capacitor up to the threshold of the logic gate. The clock establishes a time base for the sequence of operation of the microprocesser.

The voltage doubler 19 comprises a pair of capacitors disposed alternatively in parallel and in series at the clock oscillation frequency. Thus a sufficient supply voltage for the logic module 8 is obtained even when the output voltage of the clock decreases.

As illustrated in FIG. 6 the microprocessor central unit 15 comprises two registers Rp and Ri which are constituted by memories (distinct from the memory 16). The central unit further comprises an instruction decoder 26, an output circuit 27, a sequencer 28, an address register 29, an arithmetic calculator unit and logic 30 and an acumulator 31.

The instruction decoder 26 is connected by leads 32 and 33 to the registers Rp and Ri respectively, Moreover, the instruction decoder 26 is connected by a lead 34 to the bus 17 and is connected by lead 35 to the calculator unit 30 and by lead 36 to the output circuit 27.

The sequencer 28 is connected with the instruction decoder 26 by lead 37 and is connected with the address register 29 by lead 38 and with bus 17 by lead 39. The registers Rp and Ri are connected to bus 17 by leads 40 and 41 respectively. The calculator unit 30 and the accumulator 31 are connected with one another by lead 42 and are connected with bus 17 by leads 43 and 44 respectively.

The sequencer 28 is connected with the clock 18 through the voltage doubler 19 by lead 45 as illustrated in FIG. 2. The input 21 is connected to the sequencer 28 and the inputs 22 and 23 are connected to the instruction decoder 26.

The role of the instruction decoder 26 is to permit the execution of an instruction in the registers Rp and Ri through leads 32 and 33. Likewise the decoder 26 permits the execution of an instruction to the exterior of the central unit 15, notably to the output amplifier 9 through connection 14 and output circuit 27 through connection 36. The decoder 26 is connected by lead 34 to bus 17 through which it is connected with the memory 16 which contains the working programs.

The sequencer 28 is connected by lead 45 to the clock 18 through voltage doubler 19. The sequencer is thus controlled by the clock and its function is to control and organize the different operations of the central unit 15 notably the operations of the address register 29 and the instruction decoder 26. For this reason the sequencer 28 is connected to the address register 29 and to the instruction decoder 26 by leads 38 and 37. The address register 29 is connected with the memory 16 by being connected with the bus 17 by lead 39. It will be evident that the registers Rp and Ri are connected with bus 17 in order to permit direct exchange between the registers Rp and Ri and the memory 16.

The calculating unit 30 permits carrying out different logic operations of the central unit 15. The unit 30 is thus normally connected with the decoder 26 and bus 17 by leads 35 and 43 respectively. Moreover, the unit 30 is connected to the accumulator 31 which is, in fact, a secondary and permits effectively effecting the logic operations of the calculator unit 30 finally outputs 22 and 23 are connected with the instruction decoder 26.

The central unit 15 is controlled by the clock 18 through the voltage doubler 19 and lead 45. The internal control of the central unit is effected by the sequencer 28 which commands on the one hand, the instruction decoder 26 and on the other hand, the address register 29 directly associated with the memory 16 through the bus 17. The input 21 is connec-to the sequencer 28 and permits interruption if necessary.

The instruction decoder 26 thus sends instructions to the registers Rp, Ri as a function of the program found in the memory 16. The decoder 26 decodes this program and transforms it into an instruction assimable by the registers Rp and Ri.

As for external means of blocking and erasing the registers Rp and Ri this is effected by an external command by a programmer known per se which switches the unit off of a program of the memory 16 with a view to erasing the elements found in the registers Ri and Rp or of stopping the function of the apparatus.

As already mentioned hereinabove, the stimulator as described in the foregoing with its functional elements is capable of performing its normal and usual therapeutic function corresponding to a general program and also a monitoring function corresponding to a particular program.

The characteristics of the general program are as follows:

When the electrodes detect the absence of an autonomous cardiac activity, the apparatus emits stimulation pulses at a regular, known and predetermined period or rate T, notably within the range of, say, 500 to 1,300 thousandths of a second.

Whenever an autonomous or self-sustained cardiac activity is detected through the electrodes, the apparatus is recycled stimultaneously for another period T.

After each stimulation pulse, or each wave corresponding to an autonomous or self-sustained cardiac activity, a so-called "refractory" period elapses, such that any wave detected during this period is not attended by the recycling of the stimulator.

If the magnet switch 7 is closed by using external control means for example, a permanent magnet the recycling is rendered inoperative and the stimulator emits pulses continuously at said period T.

In FIG. 3, the diagram illustrates the mode of operation of the stimulator according to the general program.

In this Figure, a self-sustained wave is shown at $A_1$. If no autonomous wave follows this wave $A_1$, the stimulator, at the end of period T, will emit a stimulation pulse $S_1$. Similarly, when no self-sustained wave appears, the stimulator emits at the end of the period T following $S_1$ another stimulation pulse $S_2$. If, at the end of a time $t_1$ shorter than T an autonomous cardiac wave $A_2$ occurs, the cardiac stimulator is recycled from that time. If, after this wave $A_2$, an autonomous cardiac wave $A_3$ is produced at the end of a time $t_2$ shorter than T, the stimulator is again recycled at $A_3$. Therefore, if after $A_3$ a cardiac pause at least equal to T takes place, the stimulator will emit a stimulation pulse $S_3$ at the end of a period T following $A_3$. This pulse $S_3$ causes a refractory period having a duration $\tau$ to take place. It will be seen that the wave $s_1$ occuring after $S_3$ within the refractory period $\tau$ will not cause any recycling of the stimulator so that a stimulation pulse appears after $S_3$ at the end of period T. Similarly, the pulse 54 $S_4$ causes another refractory period having a duration $\tau$ during which a wave $S_2$ occurs which, on the one hand, does not cause any recycling of the stimulator and on the other hand brings about another refractory period of same duration, so that during this last-mentioned period a wave $S_3$, which, like $S_2$, will not recycle the stimulator, may appear.

The particular program has the following characteristics:

The first stimulation pulse is delivered after a cardiac pause due to an absence of autonomous cardiac activity during a period 2T corresponding to twice the normal stimulation period. (For example, if period T is 1,000 thousandths of second, the stimulator will wait 2,000 thousandths of second before stimulating).

After this first stimulation pulse, in the absence of any autonomous cardiac activity, a second stimulation pulse is delivered after a time 2T.

When a first pulse and a successive second pulse as just described hereinabove have been delivered, the stimulator emits successive pulses at a period T.

As long as first and second successive pulses have not been emitted, as mentioned hereinabove, the stimulator operates according to the particular program described. In contrast thereto, when the stimulator has emitted the first and second successive pulses, as mentioned hereinabove, it operates not according to the particular program but according to the general program already described in the foregoing.

FIGS. 4A and 4B illustrate two possible developments of the particular program.

In FIG. 4A, the reference symbol $A_1$ designates a self-sustained wave. In the absence of any cardiac activity, the first stimulation pulse $S_1$ appears at the end of a time 2T following $A_1$. At $A_2$ an autonomous cardiac wave appears at the end of a time of less than 2T following $S_1$, the same applying to the autonomous wave $A_3$ following $A_2$. Due to the appearance of waves $A_2$ and $A_3$, the stimulator is recycled and the stimulation pulse $S_2$ appears if a cardiac pause at least equal to 2T appears. The successive self-sustained waves $A_4$, $A_5$ and $A_6$ follow the stimulation pulse $S_2$ and will thus recycle the stimulator. In this assumption, the stimulation pulses $S_1$ and $S_2$ constitute two isolated pulses in that pulse $S_2$ does not constitute a second pulse following pulse $S_1$.

In FIG. 4B there is shown another possible mode of operation of the stimulator, in which $A_1'$ designates a self-sustained cardiac wave, and $S_1'$ is a stimulation pulse occuring after a time 2T following $A_1'$. If, after this pulse $S_1'$, no self-sustained cardiac activity appears (in contrast to the preceding case with waves $A_2$ and $A_3$ in the diagram of FIG. 4A) during a time 2T, the stimulator emits a second stimulation pulse $S_2'$ following $S_1'$, the time elapsing between these two pulses $S_1'$ and $S_2'$ corresponding to 2T. If after pulse $S_2'$ no self-sustained cardiac activity appears, and this lack of cardiac activity lasts during a time T, the stimulator will emit at $S_3'$ a stimulation pulse at the end of a period T following $S_2'$. At that time, the stimulator follows the general program so that it will normally emit pulses at said period T, in the absence of any autonomous cardiac activity. For example, there is shown at $A_2'$ a self-sustained cardiac wave taking place after $S_3'$, at the end of a time of less than T. Therefore, the stimulator is recycled after $A_2'$ and emits, for example at $S_4'$, after a time T following $A_2'$, a stimulation pulse. In this example (FIG. 4B) the stimulator has produced three successive strokes $S_1'$, $S_2'$ and $S_3'$ in conformity with the particular program. As already mentioned in the foregoing with reference to FIG. 4A, since the apparatus has not emitted successive pulses according to the particular program, it will continue its application of this particular program. On the other hand, in the case shown in FIG. 4B, the stimulator operation is switched from the particular program to the general program.

The number of stimulation pulses thus delivered is stored in the register Rp of central unit 15. More particularly, this register Rp will store:

Either the number of stimulation pulses delivered by the stimulator, if the latter has not in any case delivered at least two successive pulses, or first and second pulses according to the particular program. This case corresponds to the hypothesis illustrated in FIG. 4A. In this case, the two pulses $S_1$ and $S_2$ are registered. These two pulses correspond to the two times when a ventricular pause having a duration greater than twice and less than four times the stimulation period was observed in the patient's heart behavior. Namely, the pulse $S_1$ corresponds to the ventricular pause $A_1$, $A_2$, and the stimulation pulse $S_2$ corresponds to the ventricular pause $A_3$, $A_4$, both pauses having in fact a duration at least equal to 2T and inferior to 4T.

Let us consider the number of successive stimulation pulses delivered. This hypothesis corresponds to FIG. 4B showing three successive pulses $S_1'$, $S_2'$ and $S_3'$. This number characterizes the duration of the first ventricular pause $A_1'$, $A_2'$ which, in the case illustrated in FIG. 4B, has a duration ranging from 5T to 6T.

The values stored in register Rp are: a first isolated stimulation pulse will store "1". A second isolated stimulation pulse will store "2". A third isolated stimulation pulse will store "3", and so forth, as far as isolated stimulation pulses are concerned. If, for instance, after the third isolated stimulation pulse the apparatus emits a successive stimulation pulse, this pulse will be stored not as a "4" but as a "2". In other words, the contents of register Rp is reset to 2, when a second successive pulse is delivered. If, after this pulse, the apparatus emits other succesive pulses, these will be recorded as "3", "4", etc.

The registration ceases when one of the two following hypotheses occurs:

A self-sustained cardiac activity appears after the delivery of at least two successive stimulation pulses.

The register Rp is filled up to its rated capacity.

The register Ri of central unit 15 corresponds with register Rp and indicates whether the stimulation pulses (of which the number is recorded in Rp) are of the isolated type (case of FIG. 4A if the stimulator has not delivered two successive pulses) or of the successive type (case of FIG. 4B).

The registrations are read as follows:

With the assistance of the external disconnectable control means such as a permanent magnet, the magnetic switch 7 is actuated to its closed-citcuit position.

Then, the succession of the stimulation periods obtained is measured.

If no registrations took place, an indication of the type shown in FIG. 5A is obtained, wherein the second wave is separated from the first one by a time period 2T, and the successive waves are separated from one another by the period T.

In the case the stimulator has registered several isolated stimulation pulses, an indication as shown in FIG. 5B is obtained, which corresponds to the registration of two stimulation pulses, and in this case the following successive time lapses are obtained: 2T, 2T, 2T, T,T,T, etc.

When several successive stimulation pulses are recorded, a registration of the type illustrated in FIG. 5C is obtained for two successive pulses. In this case the pulse sequence takes place at time intervals T, 2T, 2T, T, T, etc.

It is thus obvious that by simply perusing the registration diagrams the practioner can see immediately if these correspond to successive pulses or isolated pulses. Therefore, as already explained hereinabove, it is possible to determine on the one hand the number of times the patient had a cardiac pause having a duration of more than twice and less than four times the stimulation period, and on the other hand the length of the first cardiac pause having had a duration of more than twice and less than four times the stimulation period. Consequently, from these registered elements it will be possible to check the condition and the degree of dependency of the patient in relation to his cardiac stimulator.

Moreover, externally controlled means for erasing the records and also for disconnecting the drive for the registering mechanism are provided. These means are known in the art and therefore they are not shown in the drawing or described hereinabove.

What is claimed is:

1. An implantable cardiac stimulator adapted to be associated with a cardiac probe, comprising terminals for connections with said probe, amplifier means connected with said terminals to receive and amplify a signal therefrom, band pass filter means for filtering the output of said amplifier means, level detector means receiving the filtered output signal of said filter means and operable to respond to a predetermined signal level, a logic module connected with the output of said level detector means, switch means operable by external magnetic means, said logic module comprising a central unit comprising microprocessor means including register means for recording isolated pulses and successive pulses, clock means providing a time base for said microprocessor, an OR gate having inputs connected with said level detector means and with said switch means and an output connected with said central unit, and memory means connected by a bus with said central unit, and an output stage connected with said logic module and with said terminals.

2. An implantable cardiac stimulator according to claim 1, in which said logic module further comprises voltage doubling means having an input connected with said clock means and an output connected with said switch means, central unit and memory.

3. An implantable cardiac stimulator adapted to be associated with a cardiac probe, comprising terminals for connection with said probe, amplifier means having an input connected with said terminals, band pass filter means for filtering the output of said amplifier means, level detector means receiving the filtered output signed of said filter means and operable to respond to a predetermined signal level, a logic module connected with the output of said level detector means, said logic module comprising clock means, a central unit connected with said clock means and memory means connected by a bus with said central unit and an output stage connected with said logic module and with said terminals, said central unit comprising sequencer means connected with said clock means, instruction decoder means connected with said sequencer means and with said memory means, address register means connected with said sequencer means and said memory means, register means for storing pulse patterns connected with said instruction decoder means and said memory means, logic computation means connected with said instruction decoder means and with said memory means, and means connecting said central unit with said output stage.

4. An implantable cardiac stimulator according to claim 3, in which said logic module further comprises a voltage doubler having an input connected with said clock means and an output connected with said sequencer means.

5. An implantable cardiac stimulator comprising terminals for connection with a cardiac probe, means for producing stimulation pulses cyclically at predetermined time intervals T and transmitting said stimulation pulses to said terminals, means connected with said terminals for sensing autonomous cardiac signals, means for amplifying said cardiac signals, means connected with said amplifying means for recycling said stimulation pulses when an autonomous cardiac signal appears in less than said time interval T after a stimulating pulse, means providing a refractory period after each stimulation pulse, during which period the occurence of an autonomous cardiac pulse does not cause recycling of said stimulation pulses, said refractory period being shorter than said time interval T, and means for registering successive stimulation pulses and isolated stimulation pulses for subsequent control of said stimulator.

6. An implantable cardiac stimulator an output stage having comprising two terminals for connection with a cardiac probe, a battery, two lines connecting terminals of said battery respectively with said output stage, a capacitor connected between said two lines in parallel with said battery, an amplifier connected between said two lines, a third line connecting said amplifier with one of said terminals, level detecting means connected between said two lines and having an input connected through filter means with an output of said amplifier, externally operable switch means connected in series with a resistor between said two lines, and a logic module connected between said two lines and having a first input connected with an output of said level detecting means and a second input connected between said switch means and said resistor, said output stage having an input connected with said logic module and an output connected with one of said terminals, said logic module, comprising microprocessor means, memory means connected with said microprocessor means, an OR gate having inputs connected respectively with said first and second inputs of said logic module and an output connected with said microprocessor means, clock means providing a time base for said microprocessor means and voltage doubling means connected between said clock means and said microprocessor means.

7. An implantable cardiac stimulator according to claim 6, in which said microprocessor means comprises sequencer means connected through said voltage doubler to said clock means, instruction decoder means connected with said sequencer means, two register means connected with said instruction decoder means to receive instructions from said instruction decoder means, calculating means, connected with said instruction decoder means, for carrying out logic operations of said microprocessor, accumulator means connected with said calculating means, address register means connected with said sequencer means and with said two register means, said accumulator means, said calculating means and said memory means, and output circuit means having inputs connected with said instruction decoder means and outputs connected with said output stage.

* * * * *